United States Patent [19]

Drake

[11] Patent Number: 4,736,747
[45] Date of Patent: Apr. 12, 1988

[54] ADJUSTABLE MAGNETIC SUPERCUTANEOUS DEVICE AND TRANSCUTANEOUS COUPLING APPARATUS

[75] Inventor: Gerald Ernest Drake, Oakdale, Minn.

[73] Assignee: Minnesota Mining and Manufacturing Company, St. Paul, Minn.

[21] Appl. No.: 850,868

[22] Filed: Apr. 11, 1986

[51] Int. Cl.⁴ ............................................. A61N 1/00
[52] U.S. Cl. ............................................. 128/419 R
[58] Field of Search ............... 128/654, 639, 1.3, 1 R, 128/419 R, 783; 179/107 BC, 107 E; 464/29; 128/DIG. 25

[56] References Cited

U.S. PATENT DOCUMENTS

| | | | |
|---|---|---|---|
| 3,581,742 | 6/1971 | Glenn | 128/204.19 |
| 3,814,156 | 6/1974 | Bachmann | 411/258 |
| 3,952,726 | 4/1976 | Hennig et al. | 128/DIG. 25 |
| 4,352,960 | 10/1982 | Dormer et al. | |

Primary Examiner—Kyle L. Howell
Assistant Examiner—J. P. Lacyk
Attorney, Agent, or Firm—Donald M. Sell; James A. Smith; William D. Bauer

[57] ABSTRACT

An externally worn body device adapted to be magnetically held in a supercutaneous position having a case, having a first surface adapted to be adjacent the supercutaneous position. A magnetic device is attached to the case for magnetically holding the case in the supercutaneous position. The magnetic device is moveable with respect to the distance of the magnetic device from the first surface of the case thereby allowing for adjustability in magnetic field strength at the first surface of the case. The magnetic device may be threadably attached to the case for screwably allowing movement of the magnetic device with respect to the first surface of the case. Optionally, the magnetic device may be affixed to the case once suitable adjustment has been made. The externally worn body device may further include a transmitting device positioned within the case for transmitting an electrical signal intended for transcutaneous reception. The externally worn body device may be combined with an implanted subcutaneous member which contains a magnetic device for providing an appropriate magnetic attraction to the corresponding supercutaneous magnetic device. The subcutaneous member may contain a receiving coil designed to cooperate with the transmitting coil of the externally worn body device for the reception of transcutaneous electrical signals.

14 Claims, 1 Drawing Sheet

ADJUSTABLE MAGNETIC SUPERCUTANEOUS DEVICE AND TRANSCUTANEOUS COUPLING APPARATUS

BACKGROUND OF THE INVENTION

This invention relates generally to an apparatus for coupling a member implanted in a body with a member located outside of the body. More particularly the present invention is related to magnetic devices for magnetically holding and aligning the external member supercutaneously with respect to an implanted subcutaneous member.

There exist many devices in which it is desirable to impart an electrical signal to an internal location in a body. One prime example is to facilitate electrical stimulation of the auditory nerve. In these devices, an electrode is implanted in or near the cochlea of a patient and an electrical wire transmits electrical signals to the electrode which may ultimately be interpreted by the patient as representations of sound. Other devices in which it is desirable to impart an electrical signal to an internal location in the body may include heart pacers, neuromuscular stimulators and bone growth stimulators. In each of these devices it may be necessary or desirable to impart a subcutaneous electrical signal.

In order to impart electrical signals across the skin boundary, usually either a percutaneous plug is used to directly connect the wire or else an external device is located supercutaneously proximate an implanted subcutaneous device. Percutaneous plugs generally are not desirable due to the possibility of infection. When an external supercutaneous device and an implanted subcutaneous device are used, information may be transmitted electrically across the skin boundary without requiring a direct through the skin wire connection.

Where an external supercutaneous transmitter is utilized in conjunction with an implanted subcutaneous receiver, it is important to hold the external device close to the skin boundary in order to maintain a known constant physical separation between the external transmitter and the implanted receiver. It is also important to maintain accurate lateral alignment of the transmitter and receiver with respect to each other. Errors in either of these positioning constraints can cause deteriorations in the signal being received by the implanted subcutaneous receiver.

One known mechanism for holding an external device in place is with an ear hook designed to mechanically hold the external device to the external ear. Similarly, eye glass frame structures have been used to mechanically hold an external device in place. However, in both of these cases, misalignment is common due to slippage or mechanical displacement of the mechanical device from its intended position.

Another known mechanism for holding an external device in place is described in the U.S. Pat. No. 4,352,960, Dormer et al, Magnetic Transcutaneous Mount for External Device of an Associated Implant. In Dormer, a magnetic device is located in an implanted receiver and another magnetic device is located in the external transmitter. Magnetic attraction between these two magnetic devices holds the external transmitter closely against the skin and also closely in lateral alignment. Such a system provides advantages in maintaining critical spacing and alignment of an external transmitter with a subcutaneous receiver.

Because of differences in thickness of different individual skin and differences in sensitivities to pressure against the skin, differing magnetic attractive forces for the external devices worn by differing persons are desirable. If an individual's skin thickness is greater than the norm, then the spacing between the magnetic devices is greater. In order to provide the same attractive force between the supercutaneous and subcutaneous magnetic devices, a stronger magnetic device either external or implanted is required. Since the implanted magnetic device cannot be readily changed due to the surgery involved usually in order to change the magnetic force of the supercutaneous magnetic device must be modified. Also, differences in the actual magnetic attractive force are desirable. This is because the attractive magnetic force on one individual may be comfortable but the same magnetic attractive force on another individual may cause skin irritation and soreness. It is desirable to be able to vary the magnetic attractive force in order to maintain a comfort level but still adequately hold the external device in place.

SUMMARY OF THE INVENTION

The present invention provides an externally worn body device adapted to be magnetically held in a supercutaneous position with respect to the body. The device includes a case having a first surface adapted to be adjacent the supercutaneous position. The device further has a magnetic device attached to the case for magnetically holding the case in the supercutaneous position, the magnetic device being moveable with respect to the distance of the magentic device from the first surface of the case. In a preferred embodiment, the magnetic device is attached to the case by thread means for screwably allowing the movement of the magnetic device with respect to the first surface of the case. In another preferred embodiment, the thread means are allowed to be fixed after suitable adjustment has been made, as for example, by the use of an adhesive. In another preferred embodiment, the externally worn body device further includes a transmitting device positioned within the case for transmitting an electrical signal intended for transcutaneous reception.

The present invention also provides a transcutaneous coupling apparatus. A first member is positioned subcutaneously with a first magnetic device positioned within the first member for providing an appropriate magnetic attraction to a corresponding supercutaneous magnetic member. A second member is positioned supercutaneously with a first surface adapted to be positioned adjacent the supercutaneous position. A second magnetic device is attached to the second member for magnetically holding the second member in the supercutaneous position with the second magnetic device being moveable with respect to the distance of the second magnetic device from the first surface of the second member. In a preferred embodiment, the second magnetic device is attached to the second member by thread means for screwably allowing the movement of the second magnetic device with respect to the first surface of the second member. In another preferred embodiment, the second member further includes mechanism applied to the thread means for affixing the second magnetic device in position once suitable adjustment has been made, as for example, an adhesive. In a still preferred embodiment, the transcutaneous coupling apparatus further includes a transmitting device positioned within the second member for transmitting an electrical signal intended for transcutaneous reception and a receiving device positioned within the first member for receiving the electrical signal.

In either case, the magnetic attractive force provided by the external device may be adjusted by turning the magentic device located in the externally worn body device and, thus, allowing the distance between the magnetic device and the surface of the externally worn body device closest to supercutaneous position to be adjusted by means of the threaded connection. Once adjusted the threads may be secured and further adjustment rendered in operative. Thus, the present invention provides a device which may be easily adjusted in the field for changes in skin thickness. The present invention provides a device which can be adjusted in the field for changes in magnetic field strength attraction to achieve the desired comfort level of the user. The present invention provides a highly adaptable device which eliminates the stocking of a wide variety of separate devices with differing magnetic field strengths.

BRIEF DESCRIPTION OF THE DRAWINGS

The foregoing advantages and operation of the present invention will become more readily apparent from the following description and accompanying drawings in which.

DETAILED DESCRIPTION OF THE PREFERRED EMBODIMENTS

The present invention is an improvement over the magnetic device described in U.S. Pat. No. 4,352,960, Dormer et al, Magnetic Transcutaneous Mount for External Device of an Associated Implant, which is hereby incorporated by reference.

Figure 1:
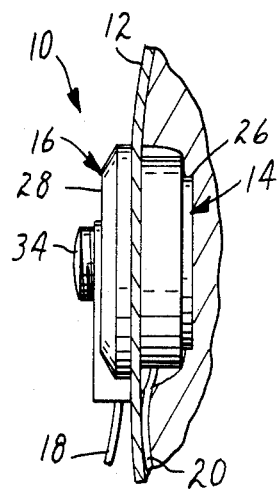
FIG. 1 is a side view of a trancutaneous coupling apparatus in place across a cutaneous boundary.

FIG. 1 illustrates the transcutaneous coupling apparatus 10 of the present invention in place across a cutaneous boundary 12 (skin). An internal device 14 is implanted subcutaneously within the body and the cutaneous boundary 12 is replaced to completely cover the internal device 14. An externally worn body device 16 is illustrated positioned supercutaneously next to the cutaneous boundary 12. In a preferred embodiment, the externally worn body device 16 contains a transmitting device designed to transmit an electrical signal designed for transcutaneous reception. The transmitting device within externally worn body device 16 receives electrical signal to be transmitted from an external processor (not shown) via electrical wire 18. In a preferred embodiment, the internal device 14 contains a receiving mechanism for receiving the transmitted cutaneous electrical signal and sending the received signal along electrical wire 20 to an electrode or other implanted device (not shown) where it can be utilized.

Figure 2:
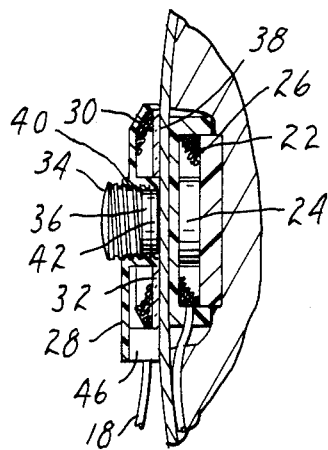
FIG. 2 is a cross-section of a transcutaneous coupling apparatus in place across a cutaneous boundary.

FIG. 2 illustrates a cross-sectional view of the same transcutaneous coupling apparatus 10 of FIG. 1. The transcutaneous coupling apparatus 10, as in FIG. 1, is shown in place across a cutaneous boundary 12. Internal device 14 is shown comprising an electrically conductive coil 22 designed to receive a transmitted electrical signal. Also, positioned within internal device 14 is magnetic device 24. In a preferred embodiment, magnetic device 24 is a permanent magnet and in a still preferred embodiment is a permanent magnet of the rare earth type. Internal device 14 is surgically implanted under the cutaneous boundary 12 in a fixed position. With respect to cochlear implants, usually this is achieved by countersinking the mastoid to receive a lip 26 of the internal device 14.

Externally worn body device 16 consists of a case 28 which in a preferred embodiment is adapted to receive an electrically conductive coil 30 coupled to wire 18 which may operate to transmit an electrical signal intended for transcutaneous reception. Securing electrically conductive coil 30 in place is coil cover 32 which may be mechanically stamped into place or held with a suitable adhesive (not shown). Electrically conductive coil 30 has a hollow core into which is inserted magnetic device 34. Case 28 contains internal threads and magnetic device 34 contains matching external threads such that magnetic device 34 may be screwed into or out of case 28 through the hollow core of coil 30. Positioned within magnetic device 34 is a magnet 36 selected to provide a suitable appropriate magnetic attraction to magnetic device 24 implanted on the other side of the cutaneous boundary 12. With magnet 36 fixed in relation to magnetic device 34, the spacing of magnet 36 to the surface 38 closest the supercutaneous position may be readily adjusted by turning the magnetic device 34 in its threaded relationship with case 28. In a preferred embodiment, it may be desirable to fix or secure the relationship of the magnetic device 34 to case 28 when appropriate adjustment has been made. In a preferred embodiment, this may be achieved by applying an adhesive 40 to the threads of magnetic device 34 and case 28. Magnet 36, which may be one or more magnetic elements, may be held in place within magnetic device 34 by magnet cover 42 which may mechanically snap into place or which may be secured by suitable adhesive (not shown). Alternatively, magnet 36 may be secured by adhesive (not shown) to magnetic device 34.

Figure 3:
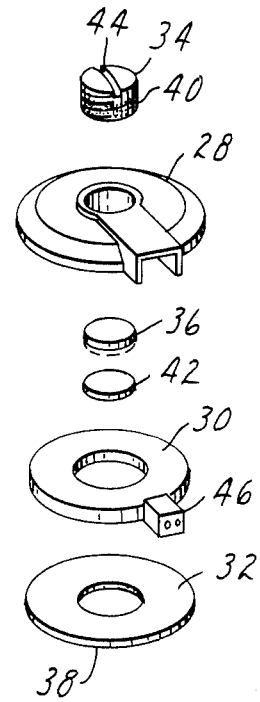
FIG. 3 is an exploded view of the external body device portion of the transcutaneous coupling apparatus.

FIG. 3 illustrates an exploded view of externally worn body device 16. Case 28 is internally threaded and adapted to receive magnetic device 34 containing external threads. The exact positioning of magnetic device 34 within case 28 may be additionally facilitated by a slot 44 in the head of magnetic device 34 to allow the use of a screwdriver or other tool to turn magnetic device 34 in threaded relationship with case 28. Magnetic device 34 receives one or more magnets 36 and is covered by magnet cover 42. Surrounding magnetic device 34 and also received into case 28 is electrically conductive coil 30 which is covered by coil cover 32. A connector 46 is provided on electrically conductive coil 30 to allow suitable connection to electric wire 18 (shown in FIG. 2). Magnetic device 34 may be secured, once adjusted, to case 28 by the use of a suitable adhesive 40 or other securing means to affix magnetic device 34 in fixed relationship with case 28.

Thus, it can be seen that there has been shown and described a novel, adjustable, magnetic, supercutaneous device and transcutaneous coupling apparatus. It is to be understood that various changes, modifications and substitutions in the form and details of the described device and apparatus can be made by those skilled in the art without departing from the scope of the invention as defined by the following claims.

What is claimed is:

1. An externally worn body device adapted to be magnetically held in a supercutaneous position in lateral alignment with a subcutaneous first magnetic element, comprising:
  a case having a first surface adapted to be adjacent said supercutaneous position;
  a second magnetic element attached to said case for magnetically holding said externally worn body device in said supercutaneous position proximate to said subcutaneous first magnetic element, holding said externally worn body device in lateral alignment with said subcutaneous first magnetic element, said magnetic element being axially aligned with said subcutaneous first magnetic element and providing direct axial magnetic attraction to said subcutaneous first magnetic element and being moveable with respect to the distance from said magnetic means to said first surface of said case for changing the magnetic field strength attraction between said second magnetic element and said subcutaneous first magnetic element.

2. An externally worn body device as in claim 1 wherein said second magnetic element is attached to said case by thread means for screwably allowing movement of said second magnetic element with respect to said first surface of said case.

3. An externally worn body device as in claim 2 which further comprises securing means applied to said thread means for affixing said second magnetic element in position once suitable adjustment has been made.

4. An externally worn body device as in claim 3 wherein said securing means comprises an adhesive.

5. An externally worn body device as in claim 2 which further comprises transmitting means positioned within said case for transmitting an electrical signal intended for transcutaneous reception.

6. An externally worn body device as in claim 2 wherein said magnetic element comprises at least one permanent magnet.

7. A transcutaneous coupling apparatus, comprising:
  a first member adapted to be positioned subcutaneously;
  a first magnetic element positioned within said first member for providing an appropriate magnetic attraction to a corresponding supercutaneous magnetic member;
  a second member having a first surface adapted to be positioned adjacent said supercutaneous position; and
  a second magnetic element attached to said second member for magnetically holding said second member in said supercutneous position with said second magnetic element in lateral alignment with said first magnetic element, said second magnetic element being moveable with respect to the distance from said second magnetic element to said first surface of said second member for changing the magnetic field strength attraction between said second magnetic element and said first magnetic element, said second magnetic element being axially aligned with said first magnetic element and providing direct axial magnetic attraction to said first magnetic element.

8. A transcutaneous coupling apparatus as in claim 7 wherein said second magnetic element is attached to said second member by thread means or screwably allowing movement of said second magnetic element with respect to said first surface of said second member.

9. A transcutaneous coupling apparatus as in claim 8 which further comprises securing means applied to said thread means for affixing said second magnetic element in position once suitable adjustment has been made.

10. A transcutaneous coupling apparatus as in claim 9 wherein said securing means comprises an adhesive.

11. A transcutaneous coupling apparatus as in claim 8 in which said second member further comprises transmitting means positioned within said second member for transmitting an electrical signal intended for transcutaneous reception and in which said first member further comprises receiving means positioned within said first member for receiving said electrical signal.

12. A transcutaneous coupling apparatus as in claim 8 wherein said first magnetic element and said second magnetic element each comprise a permanent magnet.

13. A transcutaneous coupling apparatus as in claim 11 wherein said transmitting means comprises an electrically conductive coil having a hollow core.

14. A transcutaneous coupling apparatus as in claim 13 wherein said second magnetic element is moveable within said hollow core of said conductive coil.

* * * * *